(12) United States Patent
Okuda et al.

(10) Patent No.: US 9,597,855 B2
(45) Date of Patent: Mar. 21, 2017

(54) COMPOSITE STRETCH MATERIAL AND MANUFACTURING PROCESS THEREFOR

(71) Applicant: UNICHARM CORPORATION, Ehime (JP)

(72) Inventors: Jun Okuda, Kagawa (JP); Satoshi Mitsuno, Kagawa (JP)

(73) Assignee: Unicharm Corporation, Ehime (JP)

( * ) Notice: Subject to any disclaimer, the term of this patent is extended or adjusted under 35 U.S.C. 154(b) by 59 days.

(21) Appl. No.: 14/351,188

(22) PCT Filed: Oct. 12, 2012

(86) PCT No.: PCT/JP2012/076529
§ 371 (c)(1),
(2) Date: Apr. 11, 2014

(87) PCT Pub. No.: WO2013/054923
PCT Pub. Date: Apr. 18, 2013

(65) Prior Publication Data
US 2014/0302286 A1    Oct. 9, 2014

(30) Foreign Application Priority Data
Oct. 12, 2011    (JP) ................................. 2011-225253

(51) Int. Cl.
*B32B 5/02*        (2006.01)
*B32B 3/28*        (2006.01)
(Continued)

(52) U.S. Cl.
CPC ........ *B32B 5/022* (2013.01); *A61F 13/15593* (2013.01); *A61F 13/15707* (2013.01);
(Continued)

(58) Field of Classification Search
CPC .......... A61F 13/15593; A61F 13/15707; A61F 2013/15715; B32B 3/28; B32B 38/0012;
(Continued)

(56) References Cited

U.S. PATENT DOCUMENTS

| | | | |
|---|---|---|---|
| 6,468,630 B1 | 10/2002 | Mishima et al. | |
| 2006/0270302 A1* | 11/2006 | Ando et al. | ................... 442/328 |

(Continued)

FOREIGN PATENT DOCUMENTS

| | | |
|---|---|---|
| EP | 1 166 728 A2 | 1/2002 |
| EP | 1 419 754 A1 | 5/2004 |

(Continued)

OTHER PUBLICATIONS

International Search Report from corresponding PCT application No. PCT/JO2012/076529 dated Jan. 8, 2013 (4 pgs).

*Primary Examiner* — Maria Veronica Ewald
*Assistant Examiner* — Travis Figg
(74) *Attorney, Agent, or Firm* — Brinks Gilson & Lione

(57) ABSTRACT

A composite stretch material which is composed of a first nonwoven fabric sheet part and a second nonwoven fabric sheet part and elastic members disposed therebetween. In each nonwoven fabric sheet part, concave parts and convex parts are formed in the thickness direction. The concave and convex parts formed alternately repeatedly in a first direction define convex-concave rows. The convex-concave rows are separated from each other by non-shaped regions which contain neither concave parts nor convex parts and which extend along the first direction. The non-shaped regions are joined to each other with the elastic member therebetween. The convex parts of the first nonwoven fabric sheet part enter respectively into the concave parts of the second nonwoven fabric sheet part, while the convex parts of the (Continued)

second nonwoven fabric sheet enter respectively into the concave parts of the first nonwoven fabric sheet part.

10 Claims, 9 Drawing Sheets

(51) Int. Cl.
A61F 13/15 (2006.01)
B32B 7/04 (2006.01)
B32B 38/00 (2006.01)
B32B 5/26 (2006.01)
B32B 7/12 (2006.01)
B32B 37/20 (2006.01)
B32B 37/00 (2006.01)
B32B 37/12 (2006.01)
B32B 37/14 (2006.01)
B32B 38/06 (2006.01)

(52) U.S. Cl.
CPC .................. *B32B 3/28* (2013.01); *B32B 5/26* (2013.01); *B32B 7/045* (2013.01); *B32B 7/12* (2013.01); *B32B 37/203* (2013.01); *B32B 38/0012* (2013.01); *A61F 2013/15715* (2013.01); *B32B 37/0053* (2013.01); *B32B 37/1284* (2013.01); *B32B 37/144* (2013.01); *B32B 38/06* (2013.01); *B32B 2038/0028* (2013.01); *B32B 2250/20* (2013.01); *B32B 2262/0246* (2013.01); *B32B 2262/0253* (2013.01); *B32B 2262/0276* (2013.01); *B32B 2305/20* (2013.01); *B32B 2307/51* (2013.01); *B32B 2309/105* (2013.01); *B32B 2555/02* (2013.01); *Y10T 156/1016* (2015.01); *Y10T 428/24711* (2015.01)

(58) Field of Classification Search
CPC ..... B32B 5/022; B32B 7/045; B32B 2307/51; B32B 2555/02; B32B 37/203; B32B 5/26; B32B 7/12; B32B 2038/0028; B32B 2250/20; B32B 2262/0246; B32B 2262/0253; B32B 2262/0276; Y10T 156/1016; Y10T 428/24711
See application file for complete search history.

(56) References Cited

U.S. PATENT DOCUMENTS

| | | | |
|---|---|---|---|
| 2007/0249253 | A1 | 10/2007 | Angeli et al. |
| 2009/0047855 | A1 | 2/2009 | Seth et al. |
| 2011/0251576 | A1* | 10/2011 | Ando ................ A61F 13/49011 604/385.16 |

FOREIGN PATENT DOCUMENTS

| | | |
|---|---|---|
| EP | 1 666 178 A1 | 6/2006 |
| EP | 2 039 504 A1 | 3/2009 |
| JP | 2518953 | 9/1996 |
| JP | 2001-11769 A | 1/2001 |
| JP | 2005-80859 A | 3/2005 |
| JP | 2008136667 A | 6/2008 |
| JP | 2008148834 A | 7/2008 |
| JP | 2010-536605 A | 12/2010 |

* cited by examiner

COMPOSITE STRETCH MATERIAL AND MANUFACTURING PROCESS THEREFOR

RELATED APPLICATION

This application is a 35 U.S.C. §371 national phase filing of International Patent Application No. PCT/JP2012/076529, filed Oct. 12, 2012, through which and to which priority is claimed under 35 U.S.C. §119 to Japanese Patent Application No. 2011-225253, filed Oct. 12, 2011.

TECHNICAL FIELD

The present invention relates to a composite stretch material and a manufacturing process of the same.

BACKGROUND ART

Known in the art is a composite stretch material which has two sheets and a stretch part which is comprised of a plurality of elastic members which are arranged between these two sheets, in which composite stretch material the two sheets are intermittently joined together in a stretch direction of the stretch part and a direction perpendicular to the same, the elastic members are arranged at the stretch part so as not to pass through the joined parts of the two sheets and are fastened to the two sheet materials at their two end parts, and each of the two sheets forms a plurality of folds which extend continuously along the plurality of elastic members (see PTL 1). Such a composite stretch material is soft to the touch and has a visually beautiful gather part (stretch part which has large number of folds) and can form such a gather part for absorbent products, etc.

CITATIONS LIST

Patent Literature

PTL 1. Japanese Patent Publication No. 2005-80859A

SUMMARY OF INVENTION

Technical Problem

However, in a composite stretch material which uses nonwoven fabric sheets which are not treated to shape them, when the elastic material between the nonwoven fabric sheets contracts, the nonwoven fabric sheets will deform in the thickness direction at the parts which are not joined, the thickness of the composite stretch material will increase, and thus uneven pleats will be formed. Therefore, it is difficult to obtain a thin fabric-like composite stretch member. As a result, it will not closely fit against the body of a user and an odd feeling is liable to be caused when worn.

Therefore, an object of the present invention is to provide a composite stretch material which is characterized by having a small thickness when contracted and in turn closely fitting against the body of a user and giving a good feeling and to provide a manufacturing process of the composite stretch material.

Solution to Problem

To solve the above problem, according to the present invention, there is provided a composite stretch material which is comprised of a first nonwoven fabric sheet part and second nonwoven fabric sheet part which are superposed over each other, and elastic members which are arranged between the first nonwoven fabric sheet part and the second nonwoven fabric sheet part, wherein each of the nonwoven fabric sheet parts is formed with concave parts and convex parts in a thickness direction of the nonwoven fabric sheet part, the concave parts and the convex parts are alternately repeatedly formed in a first direction and respectively extend in a second direction perpendicular to the first direction, so as to define convex-concave rows, the convex-concave rows are separated from each other by non-shaped regions which extend along the first direction without including the concave parts and the convex parts, the convex parts project out from thickness direction positions of corresponding non-shaped regions of the nonwoven fabric sheet parts, the concave parts which are formed between two of the convex parts which adjoin each other reach thickness direction positions of the non-shaped regions, the first nonwoven fabric sheet part and the second nonwoven fabric sheet part are superposed so that the non-shaped regions face each other while the convex parts of the first nonwoven fabric sheet part face the second nonwoven fabric sheet part and the convex parts of the second nonwoven fabric sheet part face the first nonwoven fabric sheet part and the elastic members are arranged in a state stretched in the first direction between the aligned non-shaped regions, the aligned non-shaped regions are joined through elastic members, and the convex parts of the first nonwoven fabric sheet part enter respectively into the insides of the concave parts of the second nonwoven fabric sheet part and the convex parts of the second nonwoven fabric sheet part enter respectively into the insides of the concave parts of the first nonwoven fabric sheet part.

Furthermore, preferably the elastic members are arranged at all of the non-shaped regions. This is because by arranging elastic members at all of the non-shaped regions, the contracting force which is applied to the composite stretch material is made more uniform over its entirety and thereby pleats can be formed more uniformly.

Furthermore, preferably the superposed first nonwoven fabric sheet part and second nonwoven fabric sheet part are joined only at the non-shaped regions and are not joined at the convex-concave rows. This is because by limiting the joined parts of the nonwoven fabric sheet to the non-shaped regions, it is possible to form pleats of shapes given to the convex-concave rows and possible to avoid large pleats from ending up being formed.

Furthermore, preferably the superposed first nonwoven fabric sheet part and second nonwoven fabric sheet part are formed at a single nonwoven fabric sheet, and the single nonwoven fabric sheet is folded along a fold line parallel to the first direction and superposed over itself. This is because it is possible to easily produce a composite stretch material from a single nonwoven fabric sheet.

Furthermore, to solve the above problem, according to the present invention, there is provided a process of manufacturing a composite stretch material which is comprised of a first nonwoven fabric sheet part and second nonwoven fabric sheet part which are superposed over each other, and elastic members which are arranged between the first nonwoven fabric sheet part and the second nonwoven fabric sheet part, the process of manufacturing a composite stretch material comprising:

a shaping step of shaping each of the nonwoven fabric sheet parts to form concave parts and convex parts in a thickness direction of the nonwoven fabric sheet parts, in which shaping step the concave parts and the convex parts are alternately repeatedly formed in a first direction and respectively extend along a second direction which is perpendicular to the first direction, so as to define convex-concave rows, the convex-concave rows are separated from each other by non-shaped regions which extend along the first direction without including the concave parts and the convex parts, the convex parts project out from thickness direction positions of corresponding non-shaped regions of the nonwoven fabric sheet parts, and the concave parts which are formed between two of the convex parts which adjoin each other reach thickness direction positions of the non-shaped regions;

an elastic member arranging step of arranging the elastic members in a state stretched in the first direction on at least one of the non-shaped regions of the first nonwoven fabric sheet part or the second nonwoven fabric sheet part;

a superposing step of superposing the first nonwoven fabric sheet part and the second nonwoven fabric sheet part so that the non-shaped regions of the first nonwoven fabric sheet part and the second nonwoven fabric sheet part face each other while the convex parts of the first nonwoven fabric sheet part face the second nonwoven fabric sheet part and the convex parts of the second nonwoven fabric sheet part face the first nonwoven fabric sheet part and making the convex parts of the first nonwoven fabric sheet part enter respectively into the insides of the concave parts of the second nonwoven fabric sheet part and the convex parts of the second nonwoven fabric sheet part enter respectively into the insides of the concave parts of the first nonwoven fabric sheet part; and a joining step of joining the non-shaped regions which are aligned through the elastic members.

Furthermore, to solve the above problem, according to the present invention, there is provided a process of manufacturing a composite stretch material which is comprised of a first nonwoven fabric sheet part and second nonwoven fabric sheet part which are superposed over each other, and elastic members which are arranged between the first nonwoven fabric sheet part and the second nonwoven fabric sheet part, the process of manufacturing a composite stretch material comprising:

a shaping step of running the nonwoven fabric sheet parts between a continuous gear roll and discontinuous gear roll which intermesh with each other while turning in opposite directions so as to form concave parts and convex parts which face a thickness direction of the nonwoven fabric sheet parts, in which shaping step the continuous gear roll has a plurality of continuous teeth which are separated from each other in a circumferential direction, each the continuous tooth continuing in a width direction, the discontinuous gear roll has a plurality of discontinuous teeth which are separated from each other in a circumferential direction, each of the discontinuous tooth being interrupted in a width direction by at least one discontinuous part, these discontinuous parts being aligned in the circumferential direction, the concave parts and the convex parts are alternately repeatedly formed in a first direction, so as to define convex-concave rows, and the convex-concave rows are separated from each other by non-shaped regions which extend along the first direction without including the concave parts and the convex parts;

an elastic member arranging step of arranging the elastic members in a state stretched in the first direction on at least one of the non-shaped regions of the first nonwoven fabric sheet part or the second nonwoven fabric sheet part;

a superposing step of superposing the first nonwoven fabric sheet part and the second nonwoven fabric sheet part so that the non-shaped regions of the first nonwoven fabric sheet part and the second nonwoven fabric sheet part face each other and so that, at the shaping step, the surfaces which are positioned at the continuous gear roll side face each other, and making the convex parts of the first nonwoven fabric sheet part enter respectively into the insides of the concave parts of the second nonwoven fabric sheet part and the convex parts of the second nonwoven fabric sheet part enter respectively into the insides of the concave parts of the first nonwoven fabric sheet part; and a joining step of mutually joining the non-shaped regions which are aligned through the elastic members.

Advantageous Effects of Invention

According to the above invention, it is possible to provide a composite stretch material which has the characteristic of being small in thickness at the time of contraction and in turn closely fitting against the body of the wearer and feeling good in touch and to provide a process of manufacturing the composite stretch material.

DESCRIPTION OF EMBODIMENTS

The present invention will be described in detail while referring to the above drawings. Note that, the figures are sometimes not drawn to the same sizes, numbers, scales, and shapes as the actual ones in order to facilitate understanding of the present invention and simplify the drawings.

The composite stretch material of the present invention is used for absorbent products such as the outer sheets, standing gather parts, etc. of disposable diapers. As an example of use of the composite stretch material of the present invention, the composite stretch material of the present invention may be used for a disposable diaper to form the torso stretch part and waist stretch part which contact the waist part and the surrounding locations of a wearer when worn. By doing this, the composite stretch material of the present invention can be particularly suitably used for locations which directly touch the skin of the wearer and where good stretchability is demanded.

Figure 1:
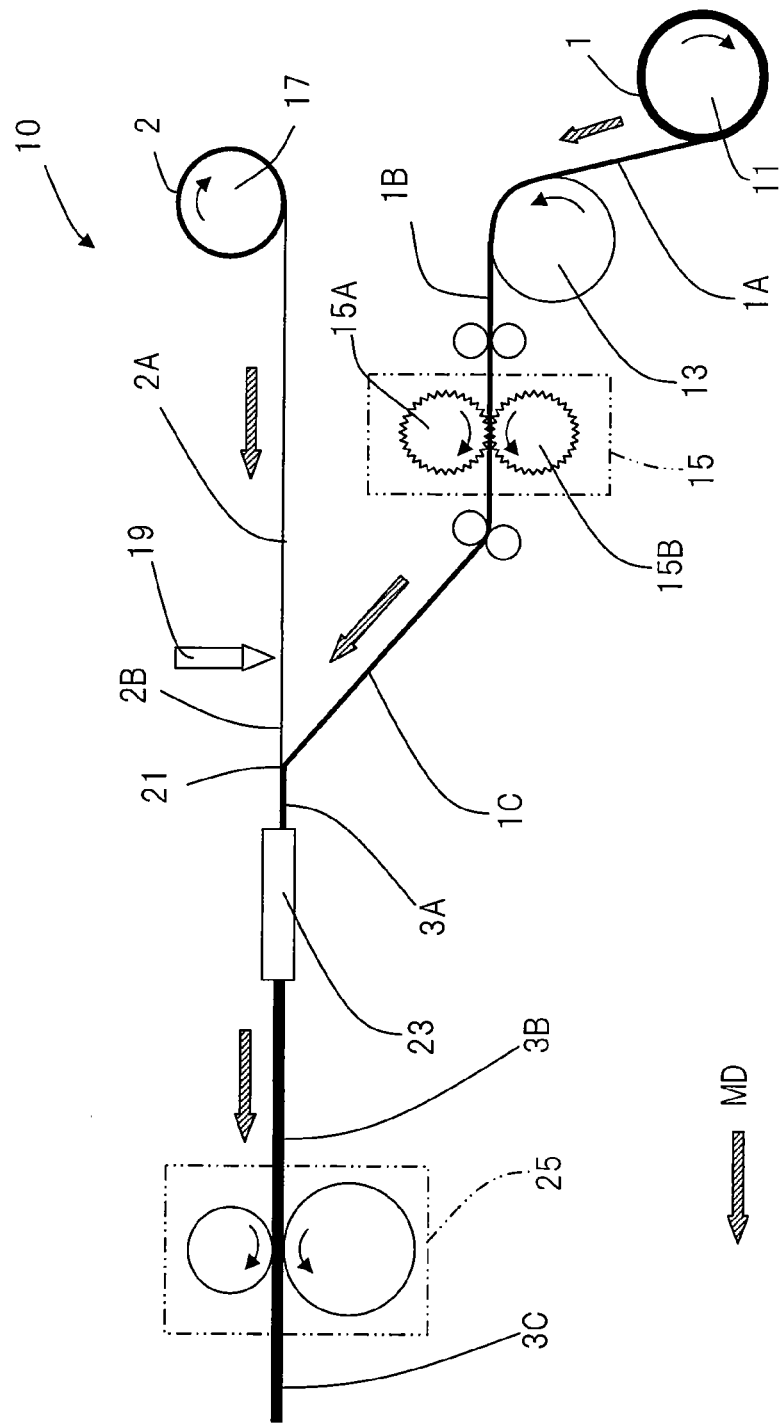
FIG. 1 is a schematic view which shows an embodiment of an apparatus for producing a composite stretch material according to the present invention.

FIG. 1 shows one embodiment of an apparatus 10 which produces the composite stretch material 3 of the present invention. Referring to FIG. 1, a nonwoven fabric sheet 1 is held with wound around a nonwoven fabric sheet feedout part 11. From there, it is unwound in a material conveyance direction (MD), that is, a first direction, and transferred to a preheating roll 13. The preheating roll 13 preheats the unwound nonwoven fabric sheet 1A to enable it to easily deform. In the present embodiment, it is set to 50 to 130° C. The preheating temperature is set in accordance with the type of the nonwoven fabric.

The preheated nonwoven fabric sheet 1B is next transferred to a shaping device 15. The shaping device 15 is comprised of a discontinuous gear roll 15A and continuous gear roll 15B. In the present embodiment, it is set in temperature to 50 to 130° C. to facilitate shaping in the same way as the preheating roll 13.

The preheated nonwoven fabric sheet 1B passes between the discontinuous gear roll 15A and the continuous gear roll 15B which intermesh with each other and rotate in opposite directions to each other. Further, as explained in detail later, it is deformed and stretched in a three-point bent shape whereby concave parts 51 and convex parts 53 which extend along a second direction which is perpendicular to the first direction are formed. Due to this, the concave parts 51 and convex parts 53 are alternately and repeatedly formed in the first direction and define convex-concave rows 41. These convex-concave rows 41 are formed at the nonwoven fabric sheet 1C while separated by non-shaped regions 43.

Figure 2:
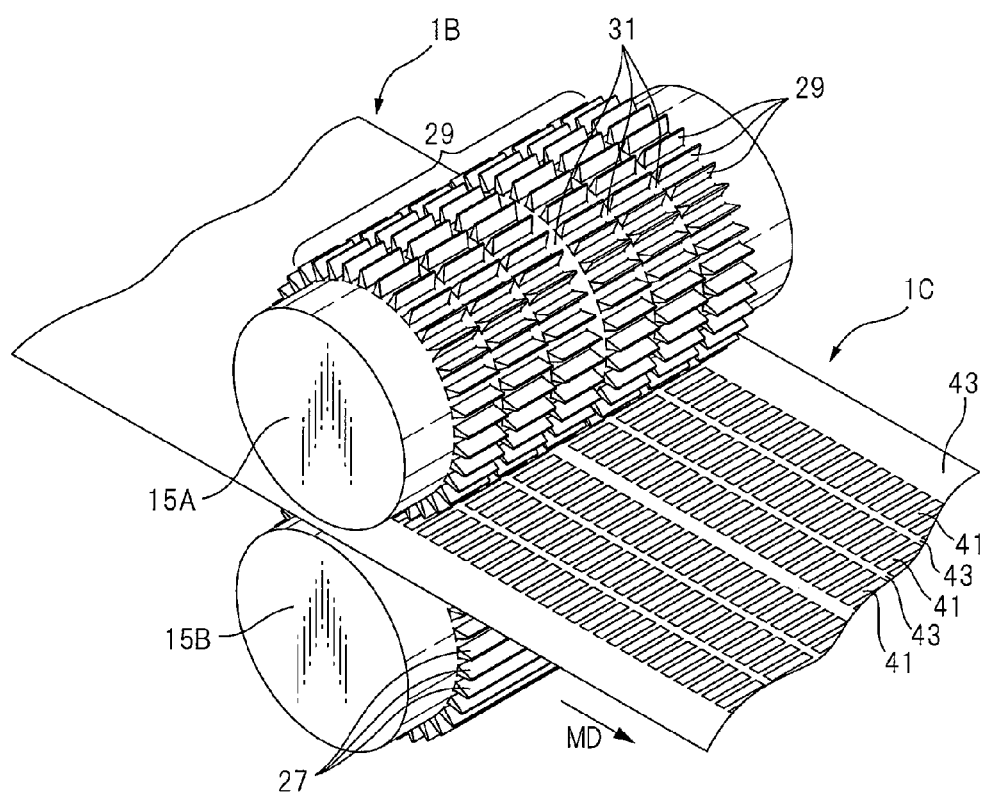
FIG. 2 is a perspective view of a discontinuous gear roll and continuous gear roll according to an embodiment.

FIG. 2 is a perspective view of a discontinuous gear roll 15A and continuous gear roll 15B according to the present embodiment and a schematic view of the nonwoven fabric sheet 10 after shaped. As shown in FIG. 2, the continuous gear roll 15B has a plurality of continuous teeth 27 which are separated from each other in the circumferential direction. Each of these continuous teeth is continuous in the width direction. Further, the discontinuous gear roll 15A has a plurality of discontinuous teeth 29 which are separated from each other in the circumferential direction. Each of these discontinuous teeth 29 is interrupted in the width direction by at least one discontinuous part 31. These discontinuous parts 31 are aligned in the circumferential direction. The preheated nonwoven fabric sheet 1B is passed between these discontinuous gear roll 15A and continuous gear roll 15B whereby the nonwoven fabric sheet 1C is formed with convex-concave rows 41 and non-shaped regions 43. In case of the present embodiment, there are five discontinuous parts 31 in each discontinuous tooth 29, but the number of discontinuous parts 31 is not limited to five and can be changed in accordance with need.

Figure 3:
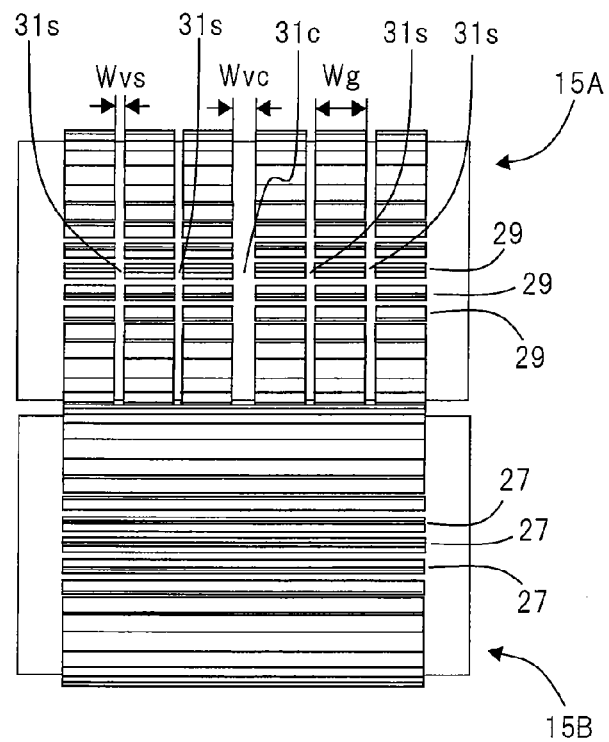
FIG. 3 is a front view of a discontinuous gear roll and continuous gear roll according to an embodiment.

FIG. 3 is a front view of a discontinuous gear roll 15A and continuous gear roll 15B. In the present embodiment, the width Wvc of the discontinuous part 31c at the center of the discontinuous gear roll 15A is 2 mm, while the widths Wvs of the discontinuous parts 31s other than the discontinuous part at the center of the discontinuous gear roll 15A are 1 mm. The widths Wg of the continuous parts of the discontinuous teeth 29 are all the same 4 mm. The center discontinuous part 31c is wider in width than the other discontinuous parts 31s because the center discontinuous part 31c becomes the part where the nonwoven fabric sheet 1 is folded in the later explained step of folding the nonwoven fabric sheet 1.

Figure 4:
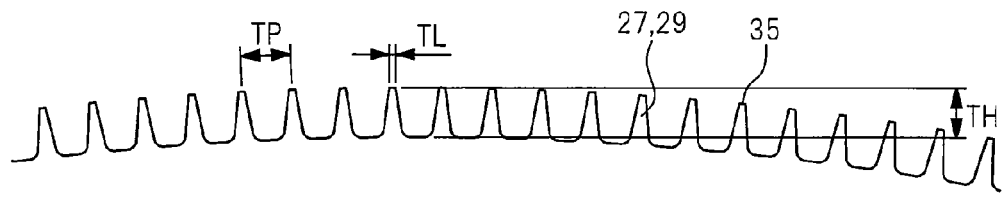
FIG. 4 is a side enlarged view of a discontinuous gear roll and continuous gear roll according to an embodiment.

FIG. 4 shows a partial side view of the discontinuous gear roll 15A and continuous gear roll 15B according to the present embodiment. In the present embodiment, the discontinuous gear roll 15A and continuous gear roll 15B have heights TH of the teeth 27 and 29 of about 1 mm, while have pitches TP between the top parts of the adjoining teeth 27 and 29 of 1 mm. Further, the teeth 27 and 29 have flat parts 35 at their tops. The flat parts 35 have lengths TL in the circumferential direction of about 0.1 mm.

Returning to FIG. 1, yarn-like elastic members 2 are stored with wound around an elastic member feedout part 17. From there, the elastic members 2 are unwound and thereby transferred to an adhesive coating part 19. The elastic members 2 are given a certain tension in advance. The later steps are performed with that tension held as it is. In the present embodiment, tension is given to the elastic members 2 so that the elastic member stretch-bond ratio (=(length of elastic material in stretched state when bonded with nonwoven fabric sheet part)÷(length of elastic material in contracted state)) is 3.

The adhesive coating part 19 coats an adhesive on the elastic members 2A which are transported from the elastic member feedout part 17.

Note that, in the present embodiment, the adhesive coating part 19 performs slit type continuous coating. The elastic members 2A run along a part discharging hot melt from a slit nozzle (not shown) so as to coat hot melt around the elastic members 2A.

Next, at a merging part 21, the elastic members 2B on which adhesive was coated are placed on the non-shaped regions 43 of the shaped nonwoven fabric sheet 1C. In the present embodiment, the nonwoven fabric sheet 1C and elastic members 2B at this stage joined together, that is, the composite stretch material 3A during production process, is shown in FIG. 5.

Figure 5:
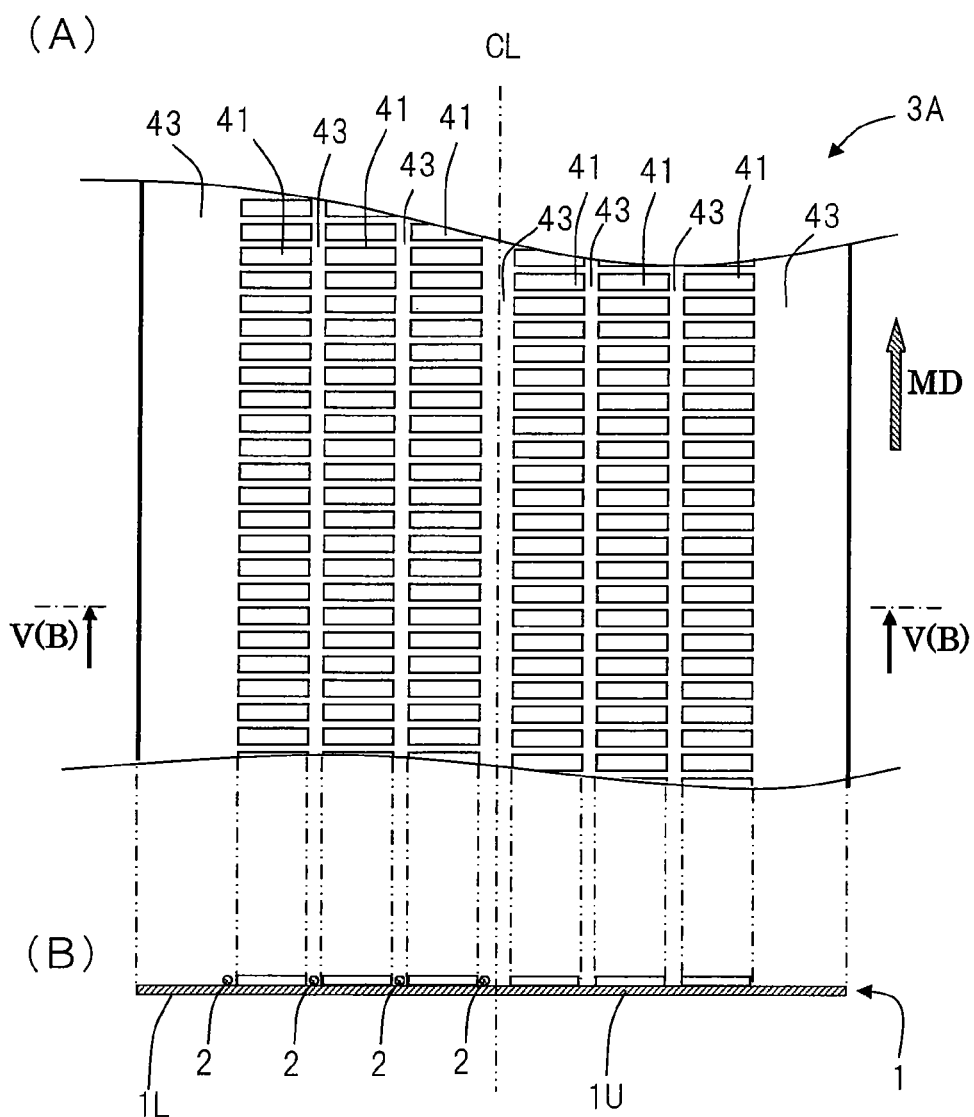
FIG. 5 is a front view and cross-sectional view of a composite stretch material before folding one nonwoven fabric sheet part by a folding apparatus.
Figure 6:
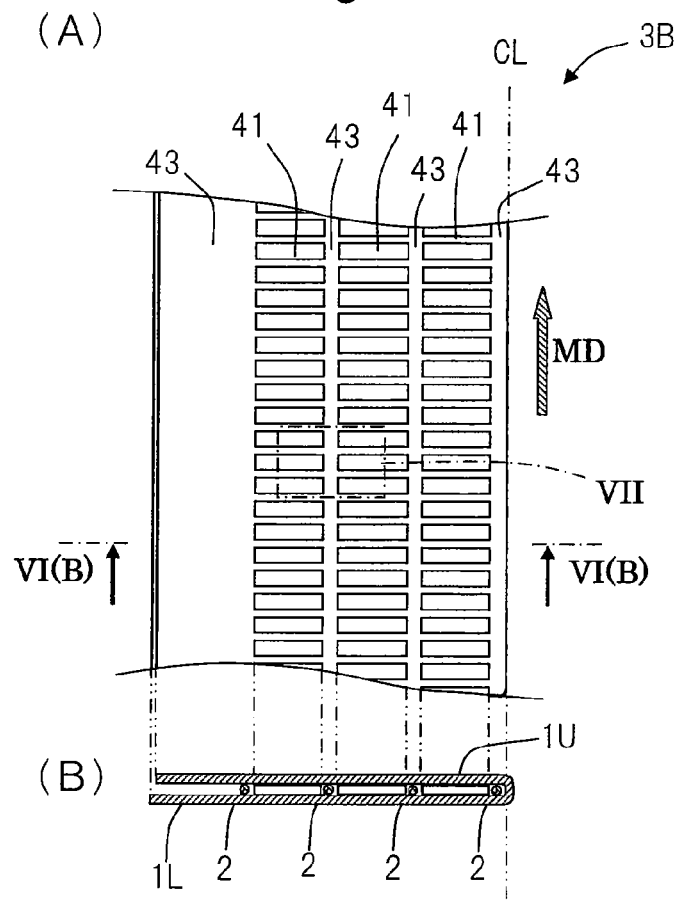
FIG. 6 is a front view and cross-sectional view of a composite stretch material after folding one nonwoven fabric sheet part by a folding apparatus.

Next, the composite stretch material 3A in the state of FIG. 5 is transferred to a folding device 23. In the present embodiment, the folding device 23 is a "rollup sailor". The rollup sailor folds the composite stretch material 3A about a centerline CL (see FIG. 5) as the fold line and superposes one side part of the nonwoven fabric sheet 1C over the other side part. Therefore, in the present embodiment, when the composite stretch material 3A in the state of FIG. 5 passes through the folding device 23, upper side nonwoven fabric sheet part 1U which is the right side half of the nonwoven fabric sheet 1 in FIG. 5 is folded at the centerline CL. Further, it is superposed on the lower side nonwoven fabric sheet part 1L which is the left side half of the nonwoven fabric sheet 1 in FIG. 5 so that the non-shaped regions 43 are aligned. As a result, the composite stretch material 3A in the state of FIG. 5 becomes the composite stretch material 3B in the state of FIG. 6.

In the present embodiment, the folding device 23 folds the material along the centerline CL, but it may also fold about any position in accordance with need so long as along a fold line parallel to the convex-concave rows 41.

Furthermore, the composite stretch material 3 according to the present embodiment is produced by superposing two nonwoven fabric sheet parts 1U and 1L of a single nonwoven fabric sheet 1, but two nonwoven fabric sheets may also be shaped separately as explained above and then superposed.

Returning to FIG. 1, finally, the composite stretch material 3B which passes through the folding device 23 is transported to a bonding press 25 where pressure is applied thereon. Due to this, the nonwoven fabric sheet parts 1U and 1L are joined at the non-shaped regions 43 through the elastic members 2B, and the final composite stretch material 3C is completed.

In the example, for the nonwoven fabric sheet 1, spunbond nonwoven fabric of a material basis weight of 17 g/m$^2$ is used. However, the present invention is not limited to this. As the nonwoven fabric which can be used, a spun bond nonwoven fabric, melt blown nonwoven fabric, heat roll nonwoven fabric, SMS nonwoven fabric which combines a spun bond nonwoven fabric and melt blown nonwoven fabric, air-through nonwoven fabric, spunlace nonwoven fabric, air-laid nonwoven fabric, etc. can be used. However, from the viewpoint of the resistance to a drop in the strength of the nonwoven fabric sheet which is required for shaping treatment, it is preferable to use a spun bond nonwoven fabric with a high degree of elongation and small difference in strength due to direction. Further, as the material of the nonwoven fabric sheet, polyethylene, polypropylene, polyester, acrylic, etc. may be used.

Further, similarly, in the example, the elastic members 2 is made of Lycra® 470DTEX. However, the present invention is not limited to this. As the elastic material used for the elastic member, urethane spandex, etc., can be used. It is preferable to use a plurality of elastic yarns with a denier of 30 to 1500 Dtex or so and to use elastic yarns with the same denier or mutually different denier. This is because if less than 30 Dtex, the number of elastic yarns used per unit width increases and the production facility may become larger, while if more than 1500 Dtex, the interval between the adjoining elastic members becomes larger and the intermeshing of the upper and lower nonwoven fabric sheet parts 1U and 1L may become uneven. Further, as the material of the elastic members, styrene-butadiene, butadiene, isoprene, neoprene, or another synthetic rubber, natural rubber, EVA, SIS, SEBS, SEPS, elastic polyolefin, polyurethane, etc. can be used.

From here, details of the composite stretch material which is produced by the above process will be explained.

Figure 7:
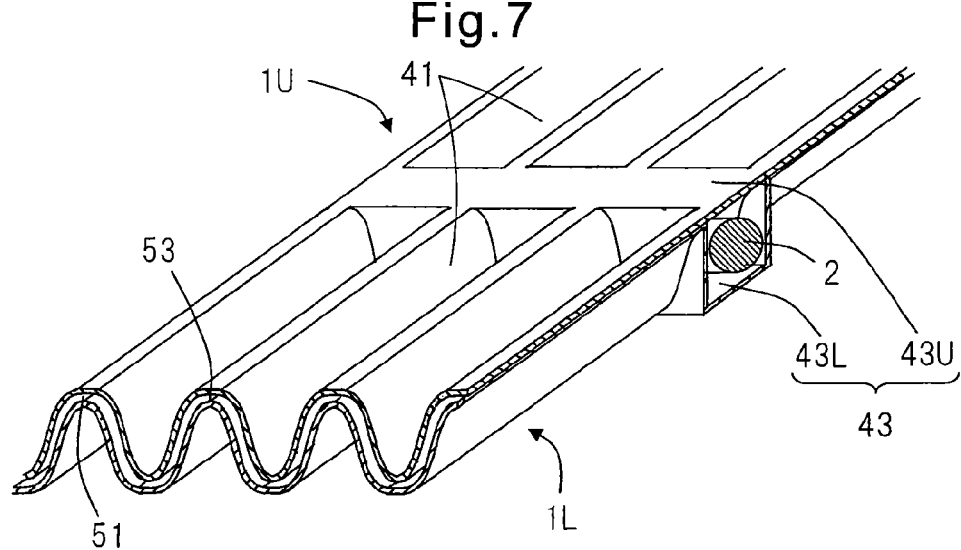
FIG. 7 is a partial enlarged perspective image view of a composite stretch material of a part cut along the line VII of FIG. 6 according to an embodiment.
Figure 8:
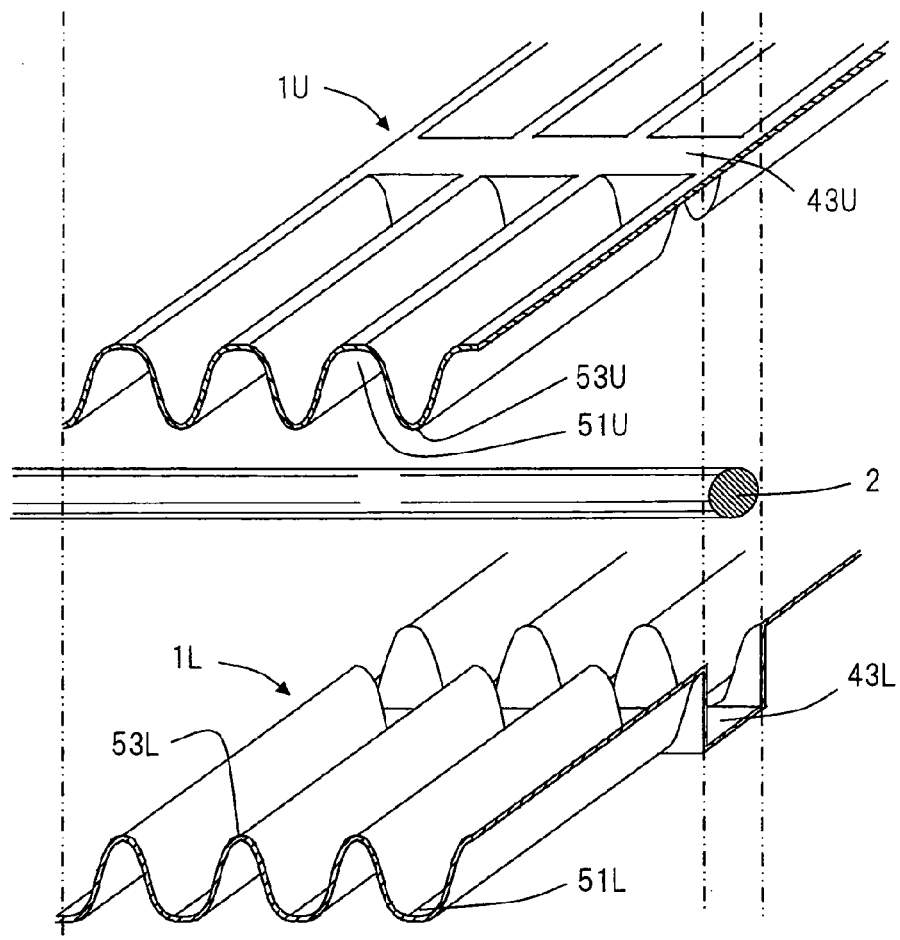
FIG. 8 is a development view of the composite stretch material of FIG. 7.

FIG. 7 is a partial enlarged perspective image view of the composite stretch material 3 which is produced by the above process, while FIG. 8 is a development view of FIG. 7.

Referring to FIG. 7 and FIG. 8, the composite stretch material 3 is comprised of the upper side nonwoven fabric sheet part 1U and the lower side nonwoven fabric sheet part 1L on which convex-concave rows 41 are formed, and elastic members 2 which are arranged between the nonwoven fabric sheet parts. The upper side nonwoven fabric sheet part 1U and the lower side nonwoven fabric sheet part 1L are as explained above formed with a plurality of straight parallel convex-concave rows 41 separated by non-shaped regions 43. The convex-concave rows 41 include the alternately repeatedly formed concave parts 51 and convex parts 53, the convex parts 53L of the lower side nonwoven fabric sheet part 1L enter respectively into the concave parts 51U of the upper side nonwoven fabric sheet part 1U, and the convex parts 53U of the upper side nonwoven fabric sheet part 1U enter respectively into the concave parts 51L of the lower side nonwoven fabric sheet part 1L.

Figure 9:
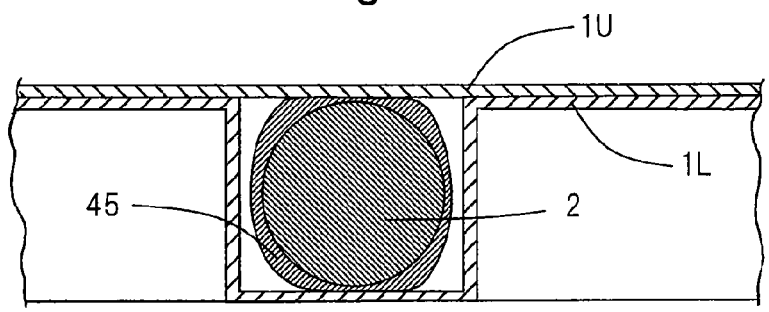
FIG. 9 is a front view of FIG. 7 which enlarges the area around the cross-section of the elastic member.

Further, FIG. 9 is a front view of FIG. 7 which enlarges the area around the cross-section of an elastic member 2. From this figure, it will be understood that with the composite stretch material 3C which is produced by the above method, the non-shaped regions 43U and 43L are joined together through the elastic members 2, more precisely, are joined by adhered parts 45 which are formed by an adhesive which is coated by the adhesive coating part 19. Note that, in FIG. 9, the adhered part 45 is distributed to cover the entire circumference of the elastic member 2, but as explained above, so long as the non-shaped regions 43U and 43L are bonded together, there is no need to cover the entire circumference of the elastic member 2.

Further, if the thickness of the composite stretch material 3 at the convex-concave rows 41 in the contracted state is greater than the diameter or cross-sectional height of the elastic members 2, when the composite stretch material 3 is touched, it becomes good in touch, so this is preferred. This is because the non-shaped regions 43 which become hard due to the adhesive which is coated around the elastic members 2 are prevented from sticking out further than the convex-concave rows 41 and the non-shaped regions 43 are therefore prevented from touching the body of the wearer before the convex-concave rows 41 and giving the wearer an odd feeling.

Figure 10A:
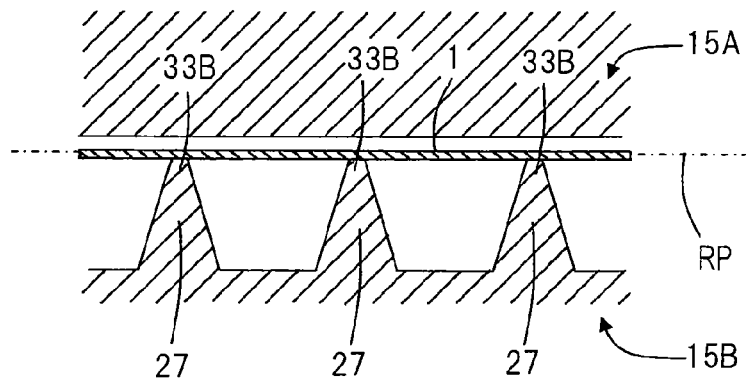
FIG. 10A is an enlarged cross-sectional image view of the area around an intermeshing part of a discontinuous gear roll and continuous gear roll and a nonwoven fabric sheet which is arranged and deformed between them at a discontinuous part of the discontinuous gear roll when laying out the discontinuous gear roll and continuous gear roll with their circumferential directions straight.
Figure 10B:
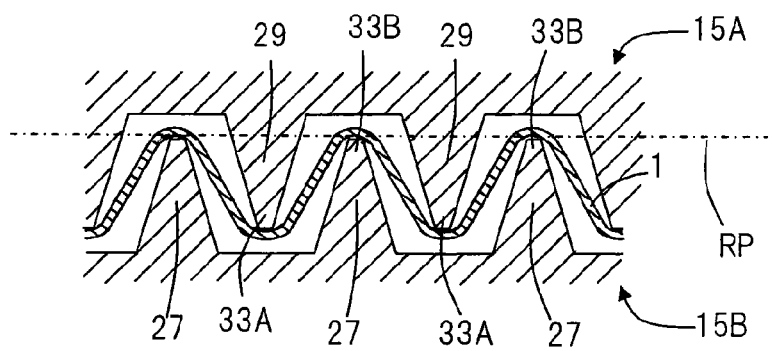
FIG. 10B is an enlarged cross-sectional image view of the area around an intermeshing part of a discontinuous gear roll and continuous gear roll and a nonwoven fabric sheet which is arranged and deformed between them at discontinuous teeth parts of the discontinuous gear roll when laying out the discontinuous gear roll and continuous gear roll with their circumferential directions straight.

Here, the mechanism by which the nonwoven fabric sheet parts 1U and 1L deform to the shapes which are shown in FIG. 7 and FIG. 8 will be explained. FIG. 10A and FIG. 10B are enlarged cross-sectional image views of the area around an intermeshing part of the discontinuous gear roll 15A and continuous gear roll 15B and the nonwoven fabric sheet 1 which is arranged and deformed between them when laying out straight the circumferential directions of the discontinuous gear roll 15A and continuous gear roll 15. FIG. 10A is a cross-sectional view at the discontinuous part 31 of the discontinuous gear roll 15A, while FIG. 10B is a cross-sectional view at a discontinuous teeth 29 part of the discontinuous gear roll 15A. Referring to FIG. 10A and FIG. 10B, on the one hand, as shown in FIG. 10A, the nonwoven fabric sheet 1 which is introduced to the discontinuous parts 31 of the discontinuous gear roll 15A is pushed against the continuous gear roll 15B to the outside in the radial direction of the continuous gear roll 15B, but does not deform and thereby forms the non-shaped regions 43. On the other hand, as shown in FIG. 10B, the nonwoven fabric sheet 1 which is caught between the discontinuous teeth 29 of the discontinuous gear roll 15A and the continuous teeth 27 of the continuous gear roll 15B are locked at the tooth front end parts 33. By doing this, the nonwoven fabric sheet 1 is stretched between each tooth front end part 33B, tooth front end part 33A and other tooth front end parts 33B which adjoin each other in a three-point bent shape whereby convex parts 53 at the tooth front end parts 33A as their top parts are formed. Furthermore, the nonwoven fabric sheet 1 is stretched between each tooth front end part 33A, tooth front end part 33B and other tooth front end parts 33A which adjoin each other in a three-point bent shape whereby concave parts 51 at the tooth front end parts 33B as their bottom parts are formed. At this time, the non-shaped regions 43 of the nonwoven fabric sheet 1 which are pushed against the continuous gear roll 15B at the discontinuous parts 31 of the discontinuous gear roll 15A and the bottom parts of the concave parts 51 of the nonwoven fabric sheet 1 which becomes locked at the tooth front end parts 33B of the continuous gear roll 15B at the discontinuous teeth 29 parts of the discontinuous gear roll 15A become substantially the same in positions in the radial directions of the gear rolls 15A and 15B. That is, the thickness direction positions in the nonwoven fabric sheet 1 are substantially identical. Accordingly, even after the nonwoven fabric sheet 1 is formed with convex-concave rows 41 and non-shaped regions 43, these are present on substantially the same plane. Here, this plane will be defined as the "reference plane RP" for the nonwoven fabric sheet parts 1U and 1L. Note that, in the present embodiment, the reference plane RP is a flat plane, and the non-shaped regions 43 extend over this reference plane RP.

Therefore, speaking in terms of the relationship between the convex parts 53 and the reference plane RP, the convex parts 53 stick out from the reference plane RP, that is, from the thickness direction position of the non-shaped regions 43.

Furthermore, here, the mechanism by which the convex parts 53 enter respectively into the concave parts 51 in the above process of manufacture will be explained.

Referring to FIG. 7, in the present embodiment, the reference planes RP of the upper side nonwoven fabric sheet 1U and the lower side nonwoven fabric sheet 1L are separated by the amount by which the convex parts 53 stick out from the reference planes RP. Therefore, a certain interval is opened between the facing non-shaped regions 43U and 43L of the upper side nonwoven fabric sheet 1U and the lower side nonwoven fabric sheet 1L. This is achieved by making one part of the shaping device 15 the discontinuous gear roll 15A and making the other part thereof the continuous gear roll 15B and thereby making the convex parts 53 stick out from the reference plane RP in only one side and by making the surfaces of the nonwoven fabric sheets 1 at the sides which have the convex parts 53 be superposed so as to face each other and in turn be superposed so that the reference planes RP of the nonwoven fabric sheets 1 are positioned at different planes outside from the composite stretch material 3. Therefore, the elastic members 2 can be placed in the spaces which are defined at certain intervals between the non-shaped regions 43U and 43L of the upper side nonwoven fabric sheet 1U and the lower side nonwoven fabric sheet 1L. In turn, by arranging the elastic members 2 between the nonwoven fabric sheet parts 1U and 1L, the action of the convex parts 53 entering respectively into the concave parts 51 is not obstructed. Note that, if there are no such spaces, it will be naturally understood that the nonwoven fabric sheet parts will not be able to approach each other by the amount of the diameters of the elastic members 2 and so the action of the concave parts entering respectively into the convex parts will be obstructed.

Furthermore, in the above process of manufacture, the entry of the convex parts 53 into the concave parts 51 can be explained as being due to the following mechanism.

A nonwoven fabric is generally soft and easy to deform, so to transport the nonwoven fabric sheet in the process of manufacture, usually a certain tension is given in a first direction, that is, the machine direction (MD). In the present embodiment, in the above process, when folding the nonwoven fabric sheet 10 of the composite stretch material 3A, a folding device 23 is used. When passing through the folding device 23, the nonwoven fabric sheet part 1U is further given tension from the folding device 23 in the first direction. Specifically, this tension is imparted by a "sailor edge" (not shown) of a rollup sailor of one specific embodiment of the folding device 23. Due to this, the upper side nonwoven fabric sheet part 1U is stretched in the first direction more than the lower side nonwoven fabric sheet part 1L. In turn, the convex-concave pitch of the convex-concave rows 41 of the upper side nonwoven fabric sheet part 1U (length of one cycle of concave parts 51 and convex parts 53 in first direction) becomes slightly greater than the convex-concave pitch of the convex-concave rows 41 of the lower side nonwoven fabric sheet part 1L. After this, when the upper side nonwoven fabric sheet part 1U is superposed on the lower side nonwoven fabric sheet part 1L, the tension is released and the state where the tension which had been applied before introduction into the folding device 23 is imparted is returned to. Next, the convex-concave pitch returns to the state before the composite stretch material 3A is introduced into the folding device 23. Therefore, the concave parts 51U and convex parts 53U of the upper side nonwoven fabric sheet part 1U and the convex parts 53L and concave parts 51L of the lower side nonwoven fabric sheet part 1L change in relative positions. As a result, when the convex-concave pitches of these parts are identical each other when the tension is released, the convex parts 53 enter respectively into the concave parts 51 with the help to the shapes of the concave parts 51 and convex parts 53.

Above, the process in the case of using a folding device was explained, but the present invention also stands even when not folding a single nonwoven fabric sheet, but separately shaping two nonwoven fabric sheets to the same shapes and superposing them as above. In this case, when superposing the nonwoven fabric sheets, one nonwoven fabric sheet is given a higher tension than the other nonwoven fabric sheet in a first direction. Due to this, it is possible to obtain the same configuration as the case of folding a single nonwoven fabric sheet.

For the above-mentioned reasons, the convex parts 53U and 53L of the nonwoven fabric sheet parts 1U and 1L enter respectively into the concave parts 51L and 51U of the nonwoven fabric sheet parts 1L and 1U.

EXAMPLES

From here, the advantageous effects of the composite stretch material according to the above-mentioned embodiment of the present invention will be explained, by using the test results of the following example and comparative examples.

The composite stretch materials of the example and comparative examples are prepared as follows:

Example 1

The composite stretch material 3 of Example 1 is a composite stretch material 3 which is produced by the process of manufacture according to the embodiment of the present invention. In the composite stretch material 3 of Example 1, at the non-shaped regions 43 between the nonwoven fabric sheet parts 1U and 1L which are shaped by the shaping device 15, elastic members 2 which are stretched so that the elastic member stretch-bond ratio becomes 3 and which are coated with an adhesive are arranged at 5 mm intervals. That is, the nonwoven fabric sheet parts 1U and 1L which are superposed so that the convex parts 53U and 53L face each other are joined at the non-shaped regions 43.

Comparative Example 1

In the composite stretch material of Comparative Example 1, between two nonwoven fabric sheet parts which are not shaped in the above way, elastic members which are stretched so that the elastic member stretch-bond ratio becomes 3 and which are coated with an adhesive are arranged at 5 mm intervals in the same way as Example 1. Due to this, the superposed nonwoven fabric sheet parts are joined with each other.

Comparative Example 2

In the composite stretch material of Comparative Example 2, at the non-shaped regions 43 between the nonwoven fabric sheet parts 1U and 1L which are shaped by the shaping device 15, elastic members which stretched so that the elastic member stretch-bond ratio becomes 3 and which are coated with an adhesive are arranged at 5 mm intervals. Further, the nonwoven fabric sheet parts 1U and 1L are folded in a direction so that the convex parts 53U and 53L face opposite directions, that is, face the outside of the finished composite stretch material, and are joined at the non-shaped regions 43. In the composite stretch material of Comparative Example 2, the nonwoven fabric sheet parts 1L and 1U are superposed in directions whereby the convex parts 53U and 53L face opposite directions, so the reference planes RP of the nonwoven fabric sheet parts 1U and 1L are arranged at substantially the same positions. As a result, the convex parts 53U and 53L of the nonwoven fabric sheet parts 1U and 1L do not enter respectively into the concave parts 51L and 51U of the nonwoven fabric sheet part 1L and 1U. This point differs from Example 1.

Further, the definitions of the measurement items and methods of the measurements are as follows: Note that these are measured in the state where the composite stretch material is contracted. This is because at the situation where such a composite stretch material is used, the composite stretch material is either in a contracted state or in a state close to a contracted state.

(Pleat Height)

Figure 11A:
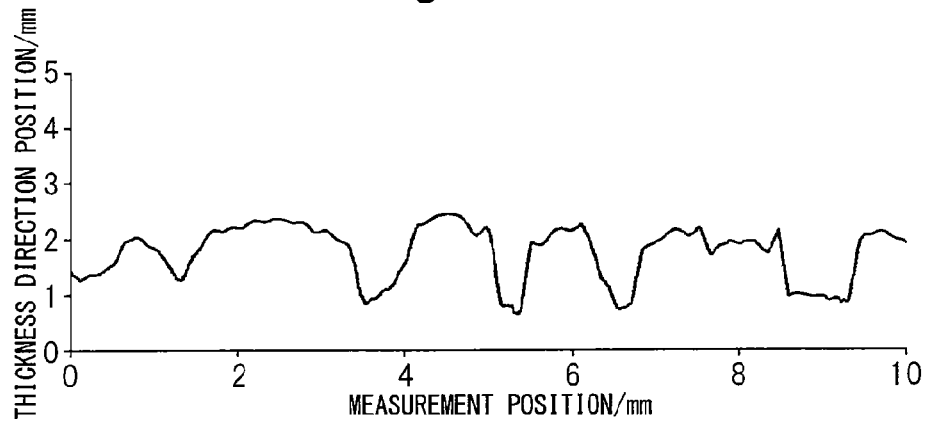
FIG. 11A is one example of a graph which shows the result of measurement of the surface shape of a composite stretch material of Comparative Example 1.
Figure 11B:
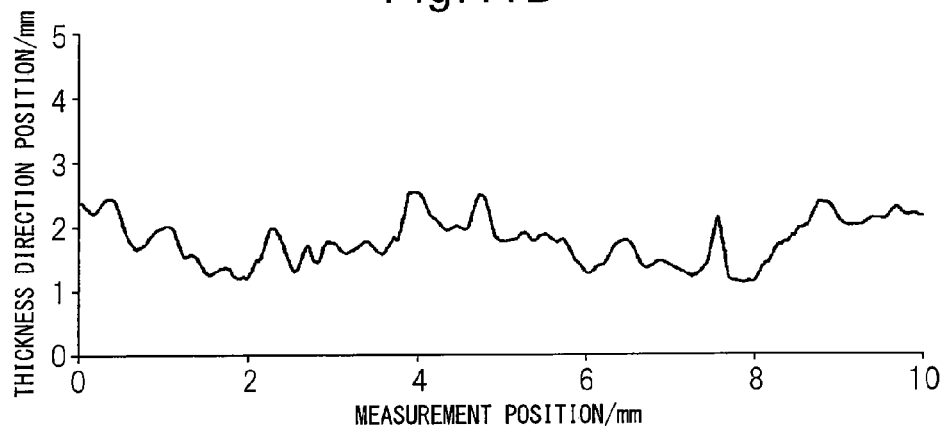
FIG. 11B is one example of a graph which shows the result of measurement of the surface shape of a composite stretch material of Comparative Example 2.
Figure 11C:
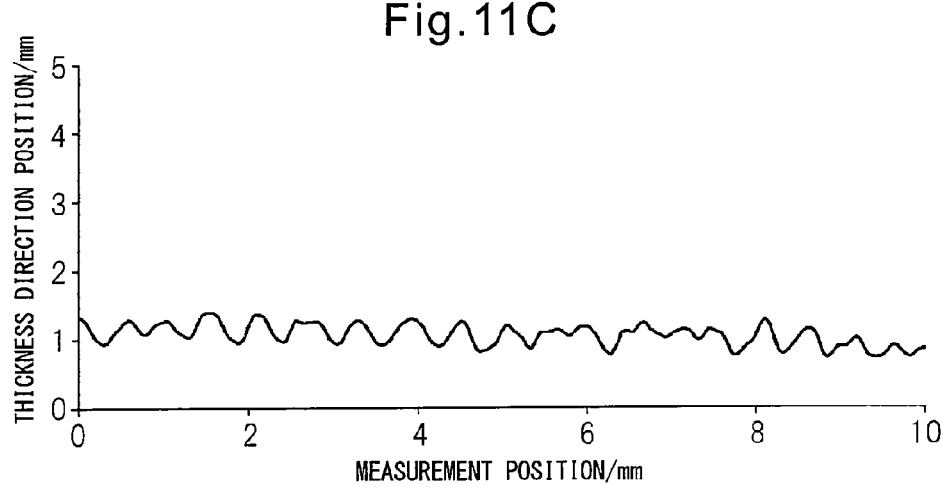
FIG. 11C is one example of a graph which shows the result of measurement of the surface shape of a composite stretch material of Example 1.

A laser shape measuring system (made by KEYENCE, KS-1100) was used to measure the surface shapes of test samples in a direction parallel to the convex-concave rows 41 so as to measure the heights of the pleats. Here, a "pleat" means a part which sticks out to one surface side over the average height of the surface shape, while the "pleat height" means the height of the highest location among the measurement points which are included in one pleat. The measurement conditions of the surface shape are a measurement range of 30 mm and a measurement pitch of 5 μm. The moving average of 12 points is taken at the stage of analysis after measurement. Examples of the measurement results of Comparative Example 1, Comparative Example 2, and Example 1 are shown in FIG. 11A, FIG. 11B, and FIG. 11C respectively.

(Average Thickness)

The "average thickness" is the average of the thicknesses of the composite stretch material measured five times when clamping a test sample in a measuring apparatus and applying 3 gf/cm$^2$ of pressure.

(Pleat Pitch)

The "pleat pitch" means the length of the nonwoven fabric sheet obtained by dividing the length of a measurement range (30 mm) by the number of pleats which are detected by a measurement.

(Pleat Density)

The "pleat density" means the number of pleats per centimeter in a direction parallel to the convex-concave rows.

The above three composite stretch materials were tested as follows:
Table 1 shows the results.

TABLE 1

|  | Comp. Ex. 1 | Comp. Ex. 2 | Ex. 1 |
| --- | --- | --- | --- |
| Average of pleat height (mm) | 1.86 | 1.79 | 1.16 |
| Standard deviation of pleat height (mm) | 0.45 | 0.43 | 0.19 |
| Average thickness of composite stretch material (mm) | 2.13 | 1.91 | 1.22 |
| Pleat pitch (mm) | 1.50 | — | 0.50 |
| Pleat density (1/cm) | 7 | — | 20 |

Referring to Table 1, in average height of pleats at the time of contraction, when compared with Comparative Example 1 and Comparative Example 2, Example 1 is clearly lower. In average thickness of the composite stretch material as well, Example 1 is clearly thinner. Therefore, the composite stretch material of Example 1 becomes thinner than those of Comparative Example 1 and Comparative Example 2 and in turn the material closely fits against the body of the wearer and can be said to be good in touch. Further, regarding the standard deviation of thickness of the pleats, Example 1 is sufficiently lower than Comparative Examples 1 and 2. Therefore, it can be understood that the composite stretch material of Example 1 forms uniform pleats as shaped in the convex-concave rows. Due to the above, the composite stretch material of Example 1 can be said to be good in touch and further excellent in aesthetic beauty. This can be understood from viewing the graphs of FIG. 11A to FIG. 11C as well. Note that, the standard deviation of the height of the pleats is preferably 0.3 or less. This is because if this extent, the material can be said to be sufficiently good in touch and is excellent in aesthetic beauty as well.

Furthermore, referring to Table 1, the pleat pitch of Example 1 is shorter than that of Comparative Example 1, while the pleat density of Example 1 is higher than that of Comparative Example 1. From this as well, it can be understood that the composite stretch material of Example 1 forms finer pleats and in turn is smaller in thickness of the composite stretch material overall. Note that, the pleat density is preferably 15 pleats/cm to 25 pleats/cm.

Furthermore, from here, using composite stretch materials changed in elastic member stretch-bond ratio, the action of the composite stretch material according to the above embodiment of the present invention will be explained using Example 1.

Figure 12:
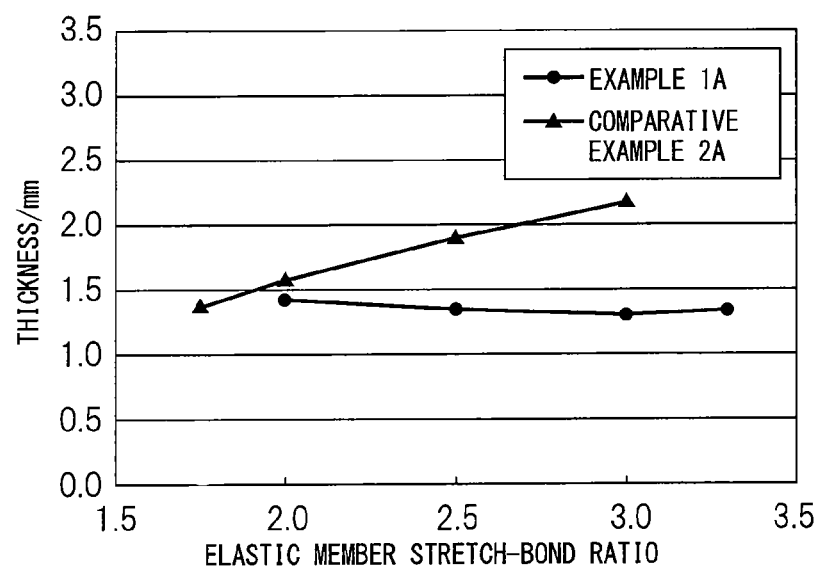
FIG. 12 is a graph which shows the thicknesses of an example and comparative example which were measured while changing an elastic member stretch-bond ratio.

FIG. 12 is a graph which shows the thicknesses of the composite stretch materials of Example 1A and Comparative Example 2A which are measured while changing the elastic member stretch-bond ratio. Note that, the composite stretch materials of Example 1A and Comparative Example 2A were prepared by changing the composite stretch materials of the above Example 1 and Comparative Example 2 in only the elastic member stretch-bond ratio.

Referring to FIG. 12, when the elastic member stretch-bond ratio is about 2, the thickness in the contracted state is pretty much no different between Example 1A and Comparative Example 2A. However, when the elastic member stretch-bond ratio increases, it will be understood that Example 1A will be smaller in thickness compared with Comparative Example 2A. When the elastic member stretch-bond ratio becomes about 3, the difference becomes more remarkable. In this way, it can be understood that the composite stretch material of the present invention does not easily become thicker in the contracted state even if increasing the elastic member stretch-bond ratio and increasing the elasticity. This is because, in Example 1A, the concave parts 51 and the convex parts 53 enter respectively into each other, so by forming pleats as shaped into the convex-concave rows, large pleats will not be formed. Therefore, even if increasing the elasticity, this action can be exhibited. This can be also understood from the results.

REFERENCE SIGNS LIST 1 nonwoven fabric sheet
1U upper side nonwoven fabric sheet part
1L lower side nonwoven fabric sheet part
2 elastic member
3 composite stretch material
15 shaping device
15A discontinuous gear roll
15B continuous gear roll
23 folding device
27 continuous teeth
29 discontinuous teeth
31 discontinuous part
41 convex-concave rows
43 non-shaped regions
51 concave parts
53 convex parts

The invention claimed is:

1. A composite stretch material which is comprised of a first nonwoven fabric sheet part and second nonwoven fabric sheet part which are superposed over each other, and elastic members which are arranged between the first nonwoven fabric sheet part and the second nonwoven fabric sheet part, wherein
  each of the nonwoven fabric sheet parts is formed with concave parts and convex parts in a thickness direction of the nonwoven fabric sheet part,
  the concave parts and the convex parts are alternately repeatedly formed in a first direction and respectively extend in a second direction perpendicular to the first direction, so as to define convex-concave rows,
  the convex-concave rows are separated from each other by non-shaped regions which extend continuously along the first direction without including the concave parts and the convex parts,
  the convex parts project out from thickness direction positions of corresponding non-shaped regions of the nonwoven fabric sheet parts,
  the concave parts which are formed between two of the convex parts which adjoin each other reach thickness direction positions of the non-shaped regions,
  the first nonwoven fabric sheet part and the second nonwoven fabric sheet part are superposed so that the non-shaped regions face each other while the convex parts of the first nonwoven fabric sheet part face the second nonwoven fabric sheet part and the convex parts of the second nonwoven fabric sheet part face the first nonwoven fabric sheet part and the elastic members are arranged in a state stretched in the first direction between the aligned non-shaped regions,
  the aligned non-shaped regions are joined through elastic members, and
  the convex parts of the first nonwoven fabric sheet part enter respectively into the insides of the concave parts of the second nonwoven fabric sheet part and the convex parts of the second nonwoven fabric sheet part enter respectively into the insides of the concave parts of the first nonwoven fabric sheet part, and wherein
  certain intervals are opened between a flat facing in the non-shaped regions of the first nonwoven sheet and the non-shaped regions of the second nonwoven fabric sheet part, and the elastic members are placed in spaces which are defined at the certain intervals between the flat facings in the non-shaped regions of the first nonwoven fabric sheet part and the non-shaped regions of the second nonwoven fabric sheet part, while the concave parts and the convex parts extended in the second direction of the convex-concave rows which are discontinued with the spaces.

2. The composite stretch material according to claim 1, wherein the elastic members are arranged at all of the non-shaped regions.

3. The composite stretch material according to claim 2, wherein the superposed first nonwoven fabric sheet part and second nonwoven fabric sheet part are joined only at the non-shaped regions and are not joined at the convex-concave rows.

4. The composite stretch material according to claim 3, wherein the superposed first nonwoven fabric sheet part and second nonwoven fabric sheet part are formed at a single nonwoven fabric sheet, and the single nonwoven fabric sheet is folded along a fold line parallel to the first direction and superposed over itself.

5. The composite stretch material according to claim 2, wherein the superposed first nonwoven fabric sheet part and second nonwoven fabric sheet part are formed at a single nonwoven fabric sheet, and the single nonwoven fabric sheet is folded along a fold line parallel to the first direction and superposed over itself.

6. The composite stretch material according to claim 1, wherein the superposed first nonwoven fabric sheet part and second nonwoven fabric sheet part are joined only at the non-shaped regions and are not joined at the convex-concave rows.

7. The composite stretch material according to claim 6, wherein the superposed first nonwoven fabric sheet part and second nonwoven fabric sheet part are formed at a single nonwoven fabric sheet, and the single nonwoven fabric sheet is folded along a fold line parallel to the first direction and superposed over itself.

8. The composite stretch material according to claim 1, wherein the superposed first nonwoven fabric sheet part and second nonwoven fabric sheet part are formed at a single nonwoven fabric sheet, and the single nonwoven fabric sheet is folded along a fold line parallel to the first direction and superposed over itself.

9. A process of manufacturing a composite stretch material which is comprised of a first nonwoven fabric sheet part and second nonwoven fabric sheet part which are superposed over each other, and elastic members which are arranged between the first nonwoven fabric sheet part and the second nonwoven fabric sheet part, the process of manufacturing a composite stretch material comprising:

a shaping step of shaping each of the nonwoven fabric sheet parts to form concave parts and convex parts in a thickness direction of the nonwoven fabric sheet parts, in which shaping step the concave parts and the convex parts are alternately repeatedly formed in a first direction and respectively extend along a second direction which is perpendicular to the first direction, so as to define convex-concave rows, the convex-concave rows are separated from each other by non-shaped regions which extend continuously along the first direction without including the concave parts and the convex parts, the convex parts project out from thickness direction positions of corresponding non-shaped regions of the nonwoven fabric sheet parts, and the concave parts which are formed between two of the convex parts which adjoin each other reach thickness direction positions of the non-shaped regions;

an elastic member arranging step of arranging the elastic members in a state stretched in the first direction on at least one of the non-shaped regions of the first nonwoven fabric sheet part or the second nonwoven fabric sheet part;

a superposing step of superposing the first nonwoven fabric sheet part and the second nonwoven fabric sheet part so that the non-shaped regions of the first nonwoven fabric sheet part and the second nonwoven fabric sheet part face each other while the convex parts of the first nonwoven fabric sheet part face the second nonwoven fabric sheet part and the convex parts of the second nonwoven fabric sheet part face the first nonwoven fabric sheet part and making the convex parts of the first nonwoven fabric sheet part enter respectively into the insides of the concave parts of the second nonwoven fabric sheet part and the convex parts of the second nonwoven fabric sheet part enter respectively into the insides of the concave parts of the first nonwoven fabric sheet part; and a joining step of joining the non-shaped regions which are aligned through the elastic members, and wherein certain intervals are opened between a flat facing in the non-shaped regions of the first nonwoven fabric sheet part and the non-shaped regions of the second nonwoven fabric sheet part, and the elastic members are placed in spaces which are defined at the certain intervals between the flat facings in the non-shaped regions of the first nonwoven fabric sheet part and the non-shaped regions of the second nonwoven fabric sheet part, while the concave parts and the convex parts extend in the second direction of the convex-concave rows which are discontinued with the spaces.

10. A process of manufacturing a composite stretch material which is comprised of a first nonwoven fabric sheet part and second nonwoven fabric sheet part which are superposed over each other, and elastic members which are arranged between the first nonwoven fabric sheet part and the second nonwoven fabric sheet part, the process of manufacturing a composite stretch material comprising:

a shaping step of running the nonwoven fabric sheet parts between a continuous gear roll and discontinuous gear roll which intermesh with each other while turning in opposite directions so as to form concave parts and convex parts which face a thickness direction of the nonwoven fabric sheet parts, in which shaping step the continuous gear roll has a plurality of continuous teeth which are separated from each other in a circumferential direction, each the continuous tooth continuing in a width direction, the discontinuous gear roll has a plurality of discontinuous teeth which are separated from each other in a circumferential direction, each of the discontinuous tooth being interrupted in a width direction by at least one discontinuous part, these discontinuous parts being aligned in the circumferential direction, the concave parts and the convex parts are alternately repeatedly formed in a first direction, so as to define convex-concave rows, and the convex-concave rows are separated from each other by non-shaped regions which extend continuously along the first direction without including the concave parts and the convex parts;

an elastic member arranging step of arranging the elastic members in a state stretched in the first direction on at least one of the non-shaped regions of the first nonwoven fabric sheet part or the second nonwoven fabric sheet part;

a superposing step of superposing the first nonwoven fabric sheet part and the second nonwoven fabric sheet part so that the non-shaped regions of the first nonwoven fabric sheet part and the second nonwoven fabric sheet part face each other and so that, at the shaping step, the surfaces which are positioned at the continuous gear roll side face each other, and making the convex parts of the first nonwoven fabric sheet part enter respectively into the insides of the concave parts of the second nonwoven fabric sheet part and the convex parts of the second nonwoven fabric sheet part enter respectively into the insides of the concave parts of the first nonwoven fabric sheet part; and a joining step of joining the non-shaped regions which are aligned through the elastic members, and wherein certain intervals are opened between a flat facing in the non-shaped regions of the first nonwoven fabric sheet part and the non-shaped regions of the second nonwoven fabric sheet part, and the elastic members are placed in spaces which are defined at the certain intervals between the flat facings in the non-shaped regions of the first nonwoven fabric sheet part and the non-shaped regions of the second nonwoven fabric sheet part, while the concave parts and the convex parts extend in the second direction of the convex-concave rows which are discontinued with the spaces.

* * * * *